United States Patent [19]

Hinshaw, Jr.

[11] Patent Number: 4,474,588

[45] Date of Patent: Oct. 2, 1984

[54] UNHEATED SEPTUMLESS ON-COLUMN INJECTION SYSTEM FOR CAPILLARY GAS CHROMATOGRAPHY

[75] Inventor: John V. Hinshaw, Jr., Martinez, Calif.

[73] Assignee: Varian Associates, Inc., Palo Alto, Calif.

[21] Appl. No.: 483,803

[22] Filed: Apr. 11, 1983

[51] Int. Cl.$^3$ ............................................. B01D 15/08
[52] U.S. Cl. ........................................ 55/197; 55/386
[58] Field of Search ................. 210/656, 198.2; 55/67, 55/197, 386

[56] References Cited

U.S. PATENT DOCUMENTS

| | | | |
|---|---|---|---|
| 3,884,802 | 5/1975 | Spaans | 210/198.2 |
| 3,902,420 | 11/1975 | Valentin et al. | 55/197 X |
| 4,124,358 | 11/1978 | Muller | 55/197 X |
| 4,269,608 | 5/1981 | Sisti et al. | 55/67 |
| 4,288,322 | 9/1981 | Guillemin et al. | 210/198.2 |

OTHER PUBLICATIONS

K. Grob, Jr. et al., "The Influence of the Syringe Needle on the Precision and Accuracy of Vaporizing GC Injections", *Jrnl of High Resolution Chromatography & Chromatographic Communications*, V.1, pp. 15-21 (1979).
F. Yang et al., "Splitless Sampling for Capillary Column Gas Chromatography", *J. Chrom.* V. 158, pp. 91-109 (1978).
A. Zlakkis et al., "Direct Sample Introduction for Large Bore Capilary Columns in Gas Chromatography", *J. Gas Chrom.*, pp. 9-11, May 1963.
G. Schomburg et al., "Sampling Techniques in Capillary Gas Chromatography", *J. Chrom.* V. 142, pp. 87-102 (1977).
K. Grob et al., "On-Column Injection Onto Glass Capillary Columns", *J. of Chromatography*, V. 151, p. 311 (1978).
K. Grob, "On-Column Injection Onto Capillary Columns", Part 2, *J. High Res Chrom & Chrom Comm.*, p. 263 (Nov. 1978).

*Primary Examiner*—John Adee
*Attorney, Agent, or Firm*—Stanley Z. Cole; Norman E. Reitz; Keiichi Nishimura

[57] ABSTRACT

An unheated septumless on-column injector with two internal flow paths is provided. A syringe means is positioned adjacent and communicates in vapor-tight relationship with the inlet ends of the two internal flow paths. The first internal flow path accepts and guides a needle from said syringe means onto the column of a gas chromatograph to permit injection onto the column. The second internal flow path allows the syringe means to either be loaded from or purged into an attached, sealed container. The needle of the syringe means is movable between the first and second paths by external manipulation. In particular embodiments, carrier gas is provided to sweep the sample into the low diameter column and cooling means is provided to ensure that the point of injection of the liquid onto the chromatographic column is maintained at a temperature below the boiling point of the most volatile component of the liquid sample.

11 Claims, 3 Drawing Figures

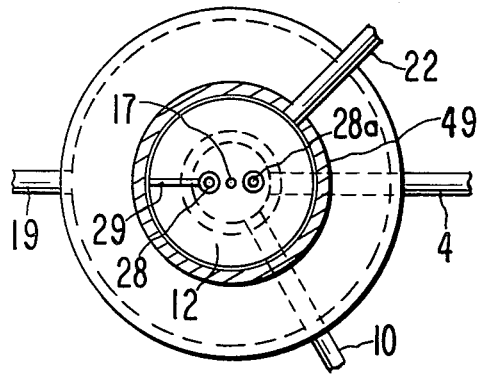
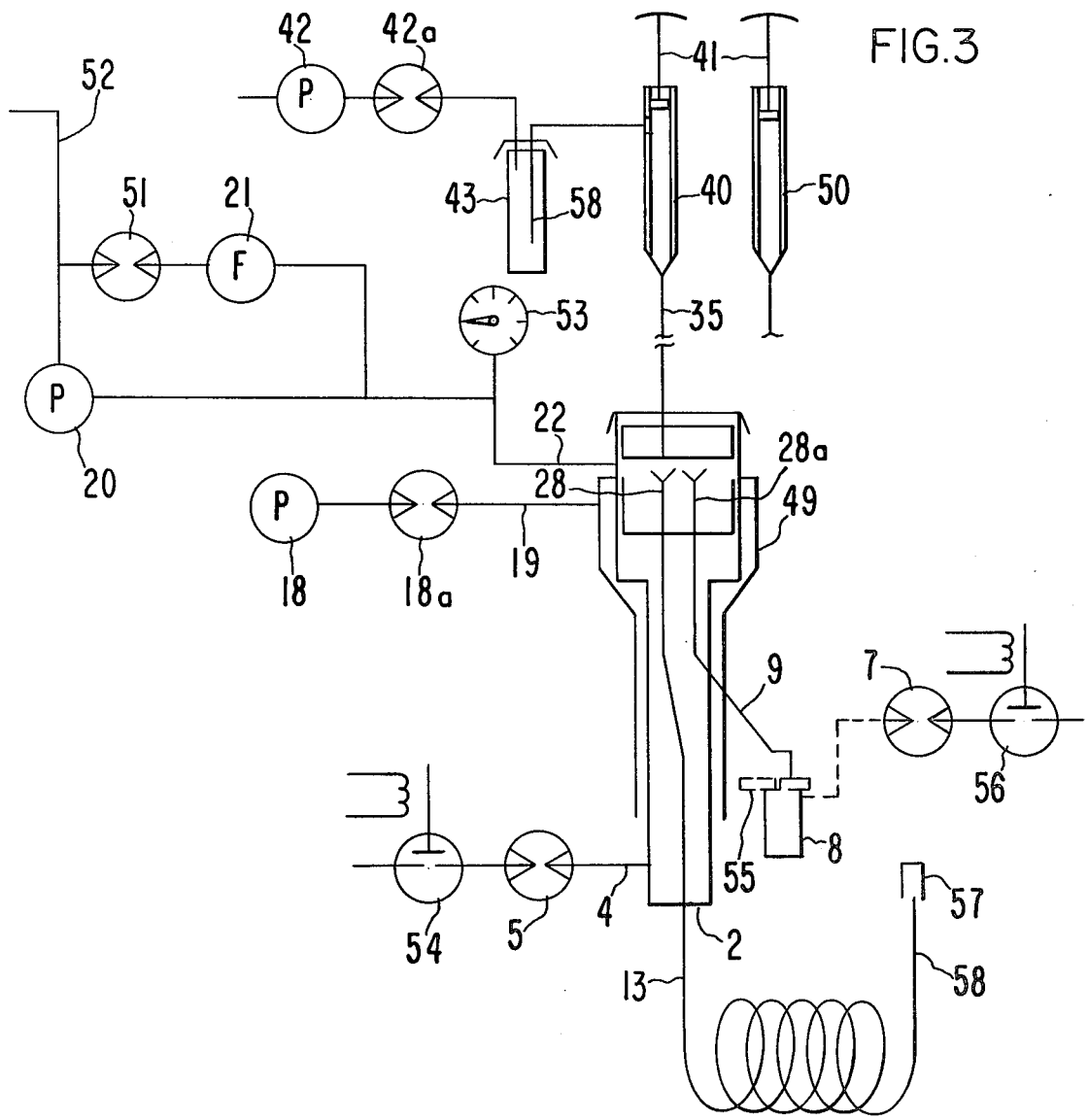

UNHEATED SEPTUMLESS ON-COLUMN INJECTION SYSTEM FOR CAPILLARY GAS CHROMATOGRAPHY

This invention relates to apparatus for injecting a sample into a gas chromatograph and, more particularly, relates to apparatus for injecting a liquid sample into the column of a gas chromatograph.

In the field of gas chromatography the introduction of the sample is a critical step. Whether the sample is initially a liquid or a gas the effluent in the chromatographic column is a gas so that one must ensure that the components of the gas do not dissociate chemically, spatially or temporally. Thus, it is a criterion for gas chromatographs that samples be introduced at a particular point at a particular time. Various approaches have been utilized to accomplish this result. With split injection a portion of the sample is introduced into the chromatograph. See, e.g., K. Grob, Jr., et al., "The Influence of the Syringe Needle on the Precision and Accuracy of Vaporizing GC Injections," *Journal of High Resolution Chromatography* and *Chromatographic Communications*, v. 1, pp. 15–21 (1979). With splitless injection the full sample is initially flowed onto the column and then the split valve is opened to purge the remaining sample. See, e.g., F. Yang, et al., "Splitless Sampling for Capillary Column Gas Chromatography," *J. Chrom.*, v. 158, pp. 91–109 (1978). With direct injection the sample is introduced into a heated region above the chromatographic column. See, e.g., A. Zlakkis, et al., "Direct Sample Introduction for Large Bore Capillary Columns in Gas Chromatography," *J. Gas Chrom.*, pp. 9–11, May 1963. With split, splitless or direct injection the portion of the sample entering the column may not always be completely representative of the original sample before entering the injection system due to effects such as thermal decomposition, mass discrimination and selective adsorption. See, e.g., G. Schomburg, et al., "Sampling Techniques in Capillary Gas Chromatography," *J. Chrom.*, v. 142, pp. 87–102 (1977). These problems have been overcome in part by so-called on-column injectors. With on-column injectors the fine needle of a syringe is inserted directly into the column and the sample is injected onto the column without exposure to an intermediate heated region. See, e.g., G. Sisti, et al., "Method and Device for Sample Injection under Controlled Conditions of Temperature Profile into Gas Chromatographic Columns", U.S. Pat. No. 4,269,608; K. Grob, et al., "On-Column Injection Onto Glass Capillary Columns", *J. of Chromatography*, v. 151, p. 311 (1978); and K. Grob, "On-Column Injection Onto Capillary Columns," Part 2, *J. High Res Chrom and Chrom Comm.*, p. 263, (Nov. 1978).

In the progressive development of injection systems for introducing samples into gas chromatographs certain desiderata have emerged. It is desirable to have a septumless injector in order to avoid contamination and so that no periodic replacement of the septum is necessary. It is also desirable to not have a heated injector which subjects the sample to high temperatures during the injection process so that unwanted vaporization of low boiling point compounds is produced; such unwanted vaporization would temporally separate high and low boiling compounds. Cold injection also eliminates dependence upon technique, i.e., the consistency and care of the operator becomes less important in determining whether good sample introduction is obtained.

It is therefore an object of the present invention to provide an injector for reliably introducing a liquid sample into the column of a gas chromatograph.

It is another object of the present invention to provide a septumless on-column injector for gas chromatography.

It is a further object of the present invention to provide an on-column injector for a gas chromatograph which does not heat the sample at the point of introduction.

It is yet another object of the present invention to provide a self-contained on-column injector which contains internal flow paths for loading injection and purging.

BRIEF DESCRIPTION OF THE DRAWINGS

For a more complete understanding of the on-column injector of the present invention reference may be had to the drawings which are incorporated herein by reference and in which:

FIG. 2 is a cross sectional view of the injector of FIG. 1 taken through lines 2—2; and FIG. 3 is a schematic diagram illustrating the pneumatics of the injector of FIGS. 1 and 2.

SUMMARY OF THE INVENTION

Figure 1:
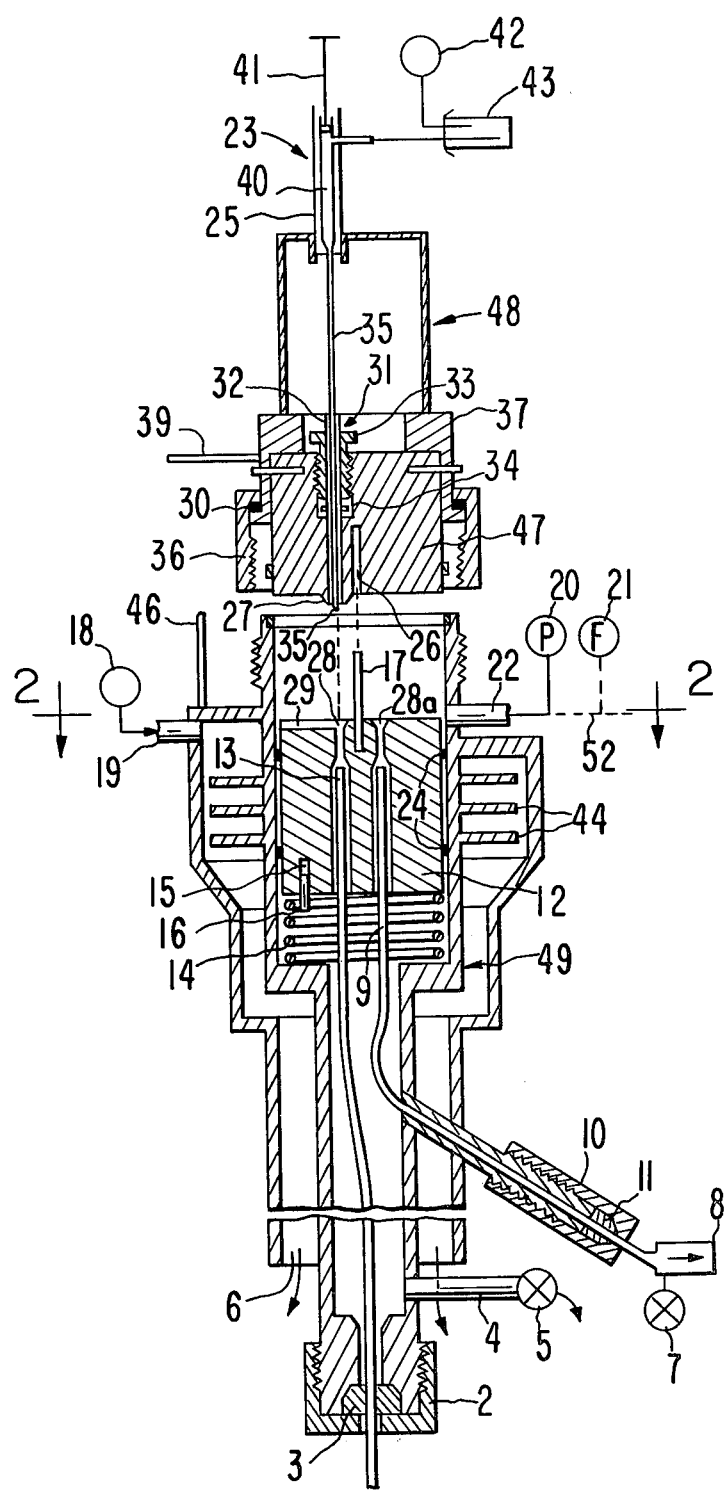
FIG. 1 is a broken away side view of one embodiment of the injector of the present invention.

An unheated septumless on-column injector with two internal flow paths is provided. A syringe means is positioned adjacent the two internal flow paths. The first internal flow path accepts and guides a needle from said syringe means onto the column of a gas chromatograph to permit injection onto the column. The second internal flow path allows the syringe means to either be loaded from or purged into an attached, sealed container. The needle of the syringe means is movable between the first and second paths by external manipulation. In particular embodiments, carrier gas is provided to sweep the sample into the low diameter column and cooling means is provided to ensure that the point of injection of the liquid onto the chromatographic column is maintained at a temperature below the boiling point of the most volatile component of the liquid sample.

DESCRIPTION OF THE PREFERRED EMBODIMENTS

The features that are desirable for a septumless, unheated on-column injection system for a gas chromatograph are incorporated in the present invention. The injector is self-contained and permits successive samples to be introduced on-column without subjecting the samples to vaporization prior to injection. The injector differs from conventional, on-column injectors in that the loading of the syringe with sample, injection and rinsing of the syringe with solvent is accomplished without removal of the syringe from the injector.

STRUCTURE

In the embodiment of the on-column injector of the present invention shown in FIG. 1, an injector body 49 contains a first interior path 28 and a second interior path 28a. A narrow column 13 such as a capillary column made from fused silica is inserted into first interior path 28. As shown, the first interior path 28 narrows at its upper end to provide a positive termination for low diameter column 13. First interior path 28 extends generally axially along the length of injector body 49. Column 13 is thus disposed axially down through injector body 49 and out an opening in ferrule 3 which is held against injector body 49 by cap 2. A length of tubing 9 nests in the neck at the upper end of second interior path 28a. The length of tubing 9 is thus disposed downwardly and generally axially through the length of injector body 49 and out through ferrule 11 which is held in place by cap 10. The tubing terminates in sealed container 8. Sealed container 8 is connected to a source of gas through valve 7 and may serve, as described below, either as a waste or sample vial.

Syringe means 23 is shown to comprise syringe body 40, plunger 41, needle 35, sliding sheath 25, and guide means 48. Sliding sheath 25 slides up and down vertically within the opening in guide 48, thereby raising or lowering needle 35 within channel 32 and thus withdrawing or inserting needle 35 in either first interior path 28 or second interior path 28a. Guide means 48 may be rotatably moved with respect to injector body 49 by turning lever arm 39. When cap 36 is fully tightened on the top of injector body 49 the movement of lever arm 309 will terminate at stop 46 so that needle 35 will be insertable precisely into first interior path 28 and onto column 13. Guide 48 rotates with respect to injector body 49 by means of bearings 30.

Within injector body 49 an insert 12 rests on coiled spring 14. Insert 12 contains passages which comprise first interior path 28 and second interior path 28a. As cap 36 is tightened onto injector body 49, pin hole 26 in cap body 47 accommodates pin 17 mounted centrally on the upper end of insert 12 in injector body 49. Since insert 12 is spring loaded it will press against the bottom of cap body 47. Then, with cap 36 fully tightened onto the top of injector body 49 and with lever arm 39 resting against a stop such as stop 46, tapered protrusion 27 on the bottom of cap body 47 nests in the beveled opening of either first interior path 28 or second interior path 28a, depending upon the angular position to which guide means 48 has been rotated by lever arm 39. As guide means 48 is rotated, protrusion 47 will contact the top of injector body 47 and translate rotational forces into linear forces with spring 14 being compressed to permit rotation of cap body 47 and guide means 40 to occur.

OPERATION

By fully withdrawing sliding sheath 25 from guide means 48, syringe needle 35 is completely withdrawn into channel 32 within the cap body 47. In this withdrawn position the rotational movement of guide means 48 above first interior path 28 and above second interior path 28a may be accomplished. This change is accomplished by rotatably moving guide means 48 until protrusion 27 is in line above the desired interior path and then lowering sliding sheath 25 until protrusion 27 is seated in the associated bevelled opening.

In operation, when protrusion 27 is seated in the bevelled opening of second interior path 28a, the needle 35 is inserted in the open end of tubing 9. In this position, providing plunger 41 is withdrawn, the syringe body 40 may be filled with sample from vial 43 by means of pressure from pressure source 42. Excess sample is then drained through tubing 9 into vial 8. The desired amount of sample is then placed into the syringe by partially depressing plunger 41 to allow the amount of sample remaining in the syringe to be the exact amount required for injection onto the column. Then, sliding sheath 25 is raised, rotatable guide means 48 is moved to position needle 35 over column 13 and sliding sheath 25 is lowered. By fully depressing plunger 41 the measured sample is injected onto the column in a discrete zone immediately below the opening of the needle. A gas-tight seal is maintained at all times. The point of injection is kept cool as cooling medium is supplied through inlet 19 from source 18. The cooling medium flows downwardly around fins 44 which contact the cooling medium and transmit heat outwardly from insert 12 and injector body 49. Cooling medium is expelled through annular conduit 6. The point of injection is thereby maintained below the temperature of the most volatile compound in the sample. Carrier gas is supplied, at least during injection, through inlet 22 from source 52 and is controlled by pressure controller 20 or flow controller 21. The carrier gas enters first interior path 28 through slot 29 (see FIG. 2) and sweeps the sample onto and through the column 13. Carrier gas is evacuated through purge outlet 4 and needle valve 5. Once the sample has been introduced, sliding sheath 23 may be slid upward, thereby raising needle 35 out of column 13 and above first interior path 28. Then, guide means 48 may be rotatably moved to rest above the bevelled opening to second interior path 28a. The relationship between the two interior paths is shown particularly in the cross-sectional view of FIG. 2. At this point, the syringe needle 35 is depressed by plunger 41 into tubing 9. Needle 35 may then be purged into container 8 by means of a solvent supplied from vial 43 which has been switched from the sample vial as, for example, could be accomplished in an autosampler.

In an alternate mode of operation the container 8 serves as a sample vial. In this embodiment a sample is drawn into syringe body 40 from vial 8 through tubing 9 when the guide means 48 is switched to alignment over second interior path 28a. In this embodiment, vial 8 represents particular ones of the vials in an autosampler.

Since the on-column injector of the present invention maintains a gas-tight seal at all times, the control of inlet pressure may be by constant flow or by constant pressure. These alternate control schemes may be seen by reference to the pneumatics diagram of FIG. 3. Pressurized inert carrier gas enters the system at point 52. For flow control, it is routed through an on-off valve 51 to a flow controller 21. For pressure control, it would be routed directly to a pressure regulator 20 of the type disclosed in D. R. Boehme, "Pressure Regulator With Minimum Dead Volume", U.S. Pat. No. 4,175,585. The flow controller and pressure regulator are connected in parallel directly to the carrier gas inlet 22, such that either pressure or flow control of the carrier gas may be used depending upon the state of valve 51. A pressure gauge 53 is provided for measuring carrier gas pressure at the inlet. Carrier gas is flowed as described previously through first and second interior paths 28 and 28a and through the column and tube inserted therein. Excess carrier gas is vented through purge outlet 4 which is provided with a needle valve 5 which is controlled by a solenoid or other on-off valve 54.

As shown in FIG. 3, the capillary column 13 enters the injector body 49 at 2, and is inserted in first interior path 28. The downstream end 58 of the capillary column 13 is connected to a suitable detector 57. For accomplishing sample injection or purging a source of gas under pressure is supplied by a pressure regulator or hand squeezed bulb 42 or the like which is connected through an on-off valve 42a such as a check valve. This source of gas administers pressure to a removable sample vial 43. Dipper tube 58, extending below the liquid level in the sample vial, connects to the side inlet of a side arm syringe 40. A conventional syringe 50 may be used in place of the side arm syringe 40, dipper tube 58, sample vial 43, on-off valve 42a and pressure source 42. Injection or purging is accomplished by depressing plunger 41 while needle 35 is inserted, respectively, in column 13 or tubing 9. A sluice valve 55 may be used for flow control of sample in a reverse embodiment where vial 8 holds sample and tubing 9 carries sample to syringe needle 35. For purging, a liquid solvent may be extracted from the injector through tubing and needle valve 7 which is controlled by solenoid assembly 56. Cooling fluid through inlet 19 is controlled by pressure regulator 18 and valve 18a.

While one embodiment for the injection system of the present invention has been disclosed, others are contemplated as within the scope of the invention. For example, the syringe means could also comprise a closed-loop injector valve such as a Rheodyne Model 7060. Various other types of syringes could be employed as long as they are capable of being inserted in the respective interior paths and onto the low diameter columns, and the movement of the syringe means with respect to the injector body could be lateral rather than rotational. Also, the interior path means could be disposed radially rather than axially. And as discussed above, various arrangements for carrier gas, sample supply and control may be employed within the context of the unheated septumless on-column injection system of the present invention.

What is claimed is:

1. An on-column injector for introducing a liquid sample onto the column of a gas chromatograph, comprising:
   an injector body having a first interior path and a second interior path, said first interior path being shaped to receive a narrow column from a gas chromatograph, said second interior path being shaped to receive a fluid transfer tubing; and
   syringe means having a channel, said syringe means being adapted to move with respect to said injector body by maintaining vapor-tight relationship therewith and to assume a first position and a second position wherein said channel is aligned respectively with said first interior path and said second interior path without exposing said first or second interior path to ambient.

2. The on-column injector of claim 1 wherein said syringe means includes a body for holding a liquid sample and a needle for insertion alternately into said first interior path for injection of said liquid sample onto said narrow column with said syringe means in said first position and for purging said body and needle with said syringe means in said second position.

3. The on-column injector of claim 2 wherein said injector body comprises a generally cylindrically shaped structure wherein said first and second interior paths are arranged generally axially within said cylindrically shaped structure and wherein said syringe means is affixed to the inlet end of said injector body, movement of said syringe means with respect to said injector body being accomplished by rotating said syringe means with respect to the inlet end of said injector body.

4. The on-column injector of claim 3 wherein said cylindrically shaped structure comprises a cylindrical shell, a cylindrical insert within said shell and a spring between the bottom of said insert and the outlet end of said housing whereby said spring loads said insert against syringe means, said insert having said first and second interior flow paths configured therein.

5. The on-column injector of claim 4 wherein each of said first and second interior flow paths have a bevelled opening formed in the top of said insert and wherein the bottom of said syringe means has a protrusion which will seat in one of said bevelled openings when said syringe means is aligned with said opening.

6. The on-column injector of claim 3 in combination with carrier gas means in gas flow communication with said first interior flow path within aid injector body for introducing carrier gas into said first interior flow path to sweep said liquid sample through said column.

7. The on-column injector of claim 3 in combination with a source vial connected to said syringe means.

8. The on-column injector of claim 3 in combination with cooling means to maintain the point of injection from said syringe means onto said column at a temperature below the boiling point of the most volatile component within said liquid sample.

9. The on-column injector of claim 8 wherein said cooling means comprises a cylindrical shroud annularly spaced apart from and surrounding said injector body and includes a source of cooling medium which medium flows through the annular region between said shroud and said injector body.

10. The on-column injector in accordance with claim 3 in combination with a capillary column within said first interior path.

11. The on-column injector in accordance with claim 3 in combination with a length of tubing within said second interior path and a sealed container in communication with the downstream end of said length of tubing.

* * * * *